United States Patent [19]

Liprie

[11] Patent Number: 5,857,956
[45] Date of Patent: *Jan. 12, 1999

[54] FLEXIBLE SOURCE WIRE FOR LOCALIZED INTERNAL IRRADIATION OF TISSUE

[75] Inventor: Samuel F. Liprie, Lake Charles, La.

[73] Assignee: United States Surgical Corporation, Norwalk, Conn.

[*] Notice: The term of this patent shall not extend beyond the expiration date of Pat. No. 5,503,614.

[21] Appl. No.: 480,307

[22] Filed: Jun. 7, 1995

Related U.S. Application Data

[63] Continuation-in-part of Ser. No. 257,045, Jun. 8, 1994, Pat. No. 5,503,614.

[51] Int. Cl.⁶ .................................................. A61M 36/00
[52] U.S. Cl. ........................................................... 600/7
[58] Field of Search ............................................ 600/1–8

[56] References Cited

U.S. PATENT DOCUMENTS

| | | |
|---|---|---|
| 3,351,049 | 11/1967 | Lawrence . |
| 4,763,642 | 8/1988 | Horowitz . |
| 4,819,618 | 4/1989 | Liprie . |
| 4,861,520 | 8/1989 | Van't Hooft et al. . |
| 4,891,165 | 1/1990 | Suthanthiran . |
| 5,084,002 | 1/1992 | Liprie . |
| 5,141,487 | 8/1992 | Liprie . |
| 5,163,896 | 11/1992 | Suthanthiran et al. ................... 600/8 |
| 5,199,939 | 4/1993 | Dake et al. . |
| 5,282,781 | 2/1994 | Liprie . |
| 5,342,283 | 8/1994 | Good . |
| 5,354,257 | 10/1994 | Roubin et al. . |
| 5,503,614 | 4/1996 | Liprie ........................................ 600/8 |

FOREIGN PATENT DOCUMENTS

| | | |
|---|---|---|
| WO 93/04735 | 3/1993 | WIPO . |
| 9425106 | 11/1994 | WIPO . |

OTHER PUBLICATIONS

Flexdmedics, "Nitinol . . . The material of choice for safer, more effective medical procedures", Advertisement literature, 3 pages, 1989.

*Primary Examiner*—John P. Lacyk
*Assistant Examiner*—Samuel Gilbert

[57] ABSTRACT

A flexible source wire is provided containing a radioactive source that is capable of maneuvering through a tortuous narrow passage to a treatment site within the body. This source wire includes a thin flexible housing tube, housing therein a flexible backbone wire, wherein both the tube and the wire are constructed from a material exhibiting little or no memory retention when bent. A radioactive core is provided in the proximal end (i.e., the treatment end) of the thin flexible housing tube and abuts the proximal end of the backbone wire. Both ends of the source wire are sealed and the proximal end of the source wire is rounded to allow ease of movement as it travels through the bends and turns in the body.

98 Claims, 7 Drawing Sheets

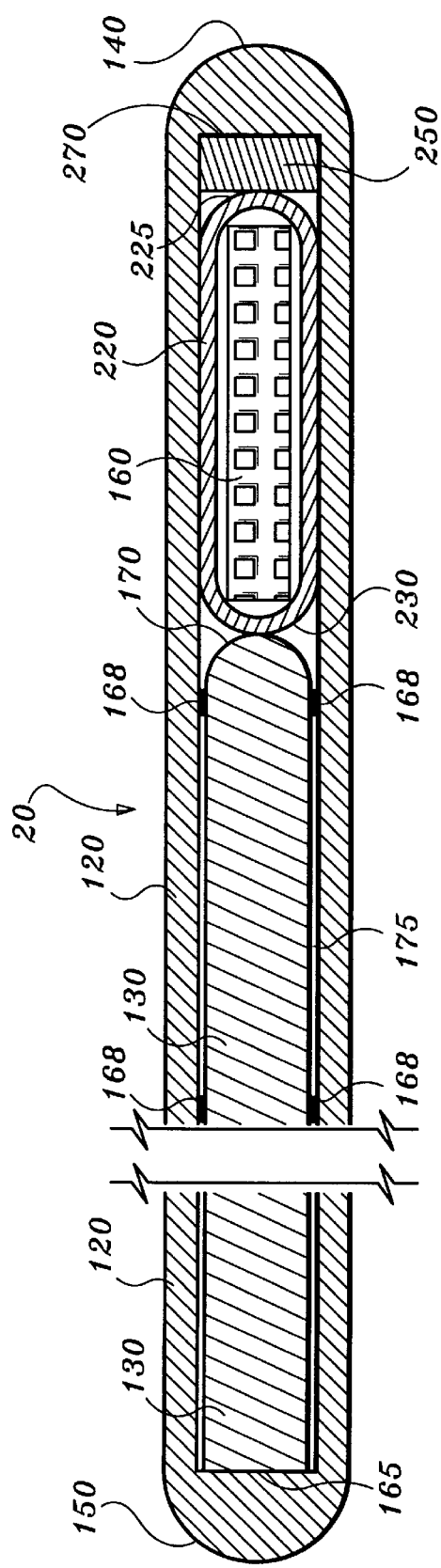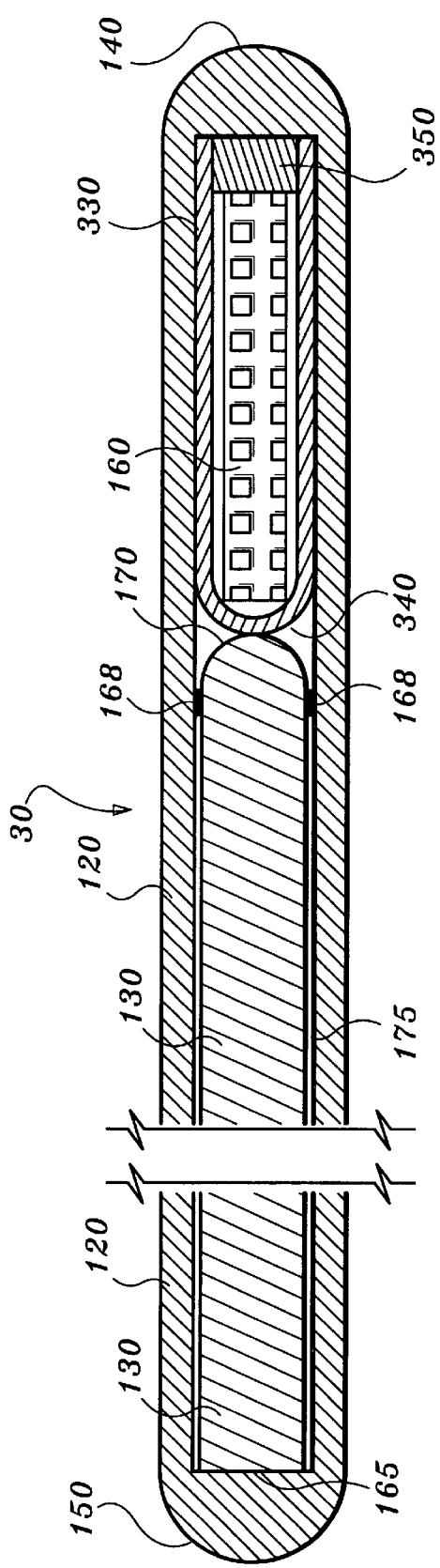

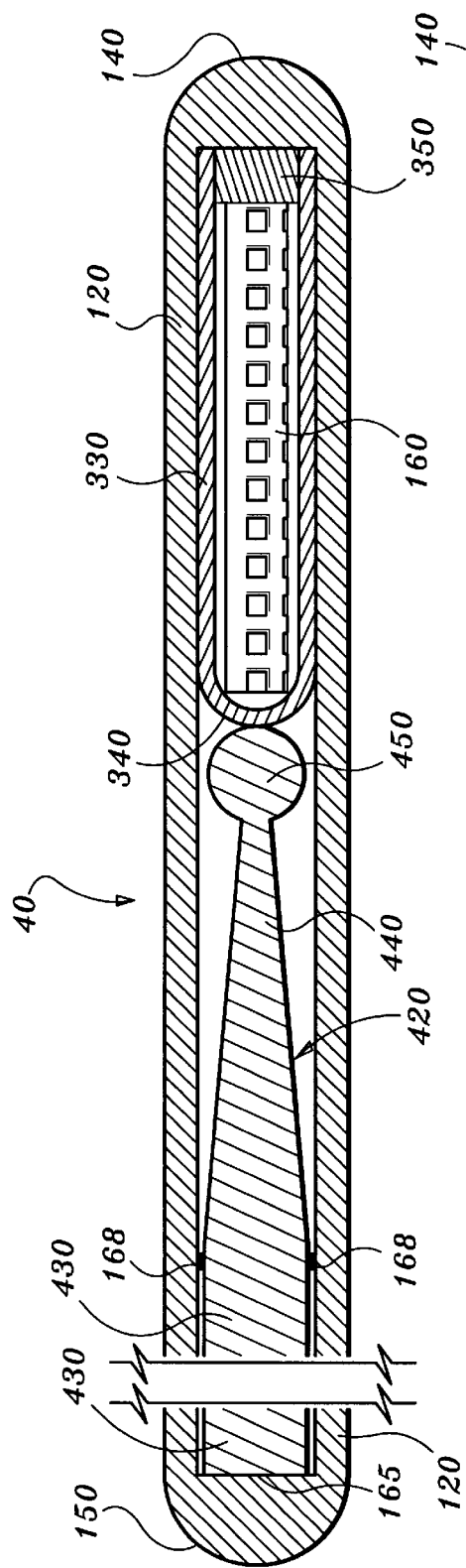
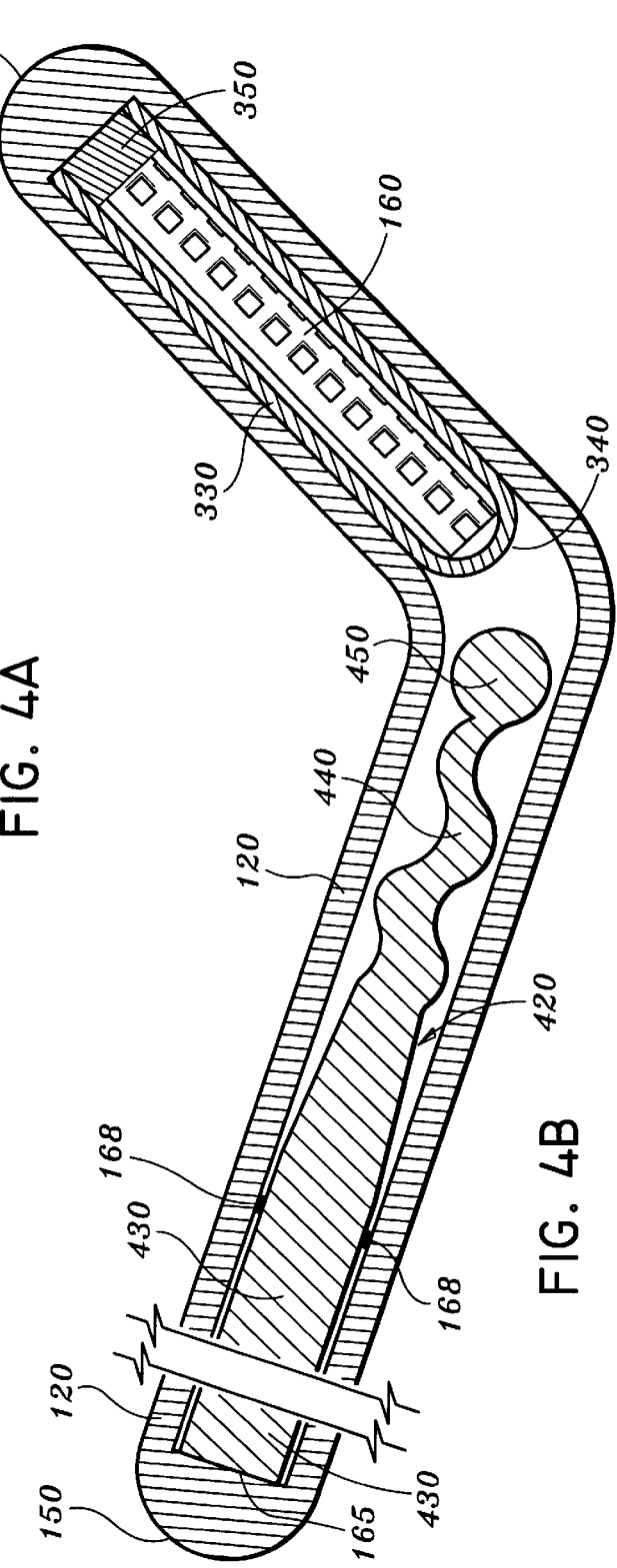

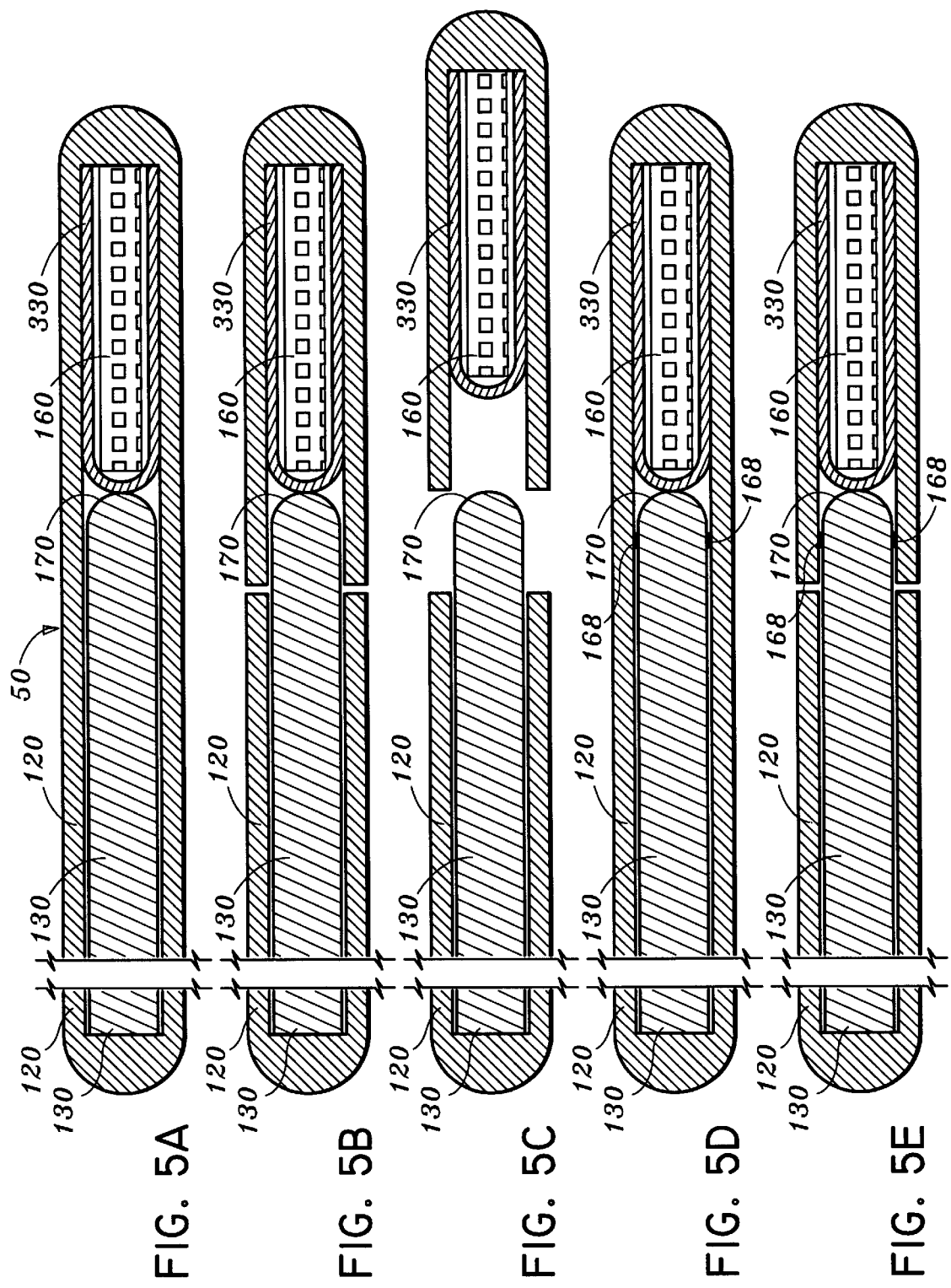

FLEXIBLE SOURCE WIRE FOR LOCALIZED INTERNAL IRRADIATION OF TISSUE

REFERENCE TO RELATED PATENT APPLICATIONS

The present application is a continuation-in-part of U.S. application Ser. No. 08/257,045 filed Jun. 8, 1994 and entitled "Flexible Source Wire for Radiation Treatment of Diseases," the entire contents and disclosure of which are hereby specifically incorporated by reference now U.S. Pat. No. 5,503,614.

FIELD OF THE INVENTION

The present invention relates generally to radioactive source wires used to irradiate body tissue in the treatment of disease. More particularly, the present invention relates to the use of an elongated radioactive source wire with increased flexibility for the localized delivery of radiation to diseased tissue.

BACKGROUND OF THE INVENTION

Radiation is used to treat cancer and other diseases of the body. Radiation has long been proven to destroy fast multiplying cells (e.g., cancer) in hopes of destroying or preventing the spread of the disease. Brachytherapy, which is the treatment of cancer at close distances, is one example of the use of radiation for treating diseases of the body. During brachytherapy, a radioactive source or sources are positioned in the area needing treatment. Depending on the shape, size and delivery means of the radioactive sources, the sources are either kept permanently in the body or removed after a specific amount of time. Since permanent implants are tiny seeds approximately 3 mm long and 0.5 mm wide, the use of these seeds do not relate to the present invention. Consequently, the focus of this application will be on the field of temporary implants.

The term temporary implants describes the procedure of maneuvering a radioactive source or sources to the treatment site utilizing a transport catheter or tube which has been previously placed in the vicinity of this treatment site. Alternatively, the transport catheter and temporary implant can simultaneously be maneuvered to the treatment site. In either situation, after a specified period of time, these sources and the transport catheter or tube are removed from the body. Since the radioactive source or sources may encounter a tortuous path in various arteries, veins, ducts, or the like inside the body to reach the treatment site, the radioactive source is usually attached by some device to a flexible drive member. This source and the drive member may be used many times, and, therefore must be able to withstand the many bends it encounters when it is maneuvered to the treatment site or removed therefrom, without breaking.

There are several devices on the market in which radioactive sources are attached to flexible drive members. Each of these devices is constructed in a different fashion and each has its limitations. Examples of these prior art devices are described in U.S. Pat. Nos. 4,819,618 and 5,141,487, both issued to Liprie as well as U.S. Pat. No. 4,861,520 issued to van't Hooft. The two Liprie patents describe a radioactive element which is attached to a drive member by means of a junction welded to the drive cable. The patent to van't Hooft describes an apparatus which attaches radioactive sources to a drive cable by means of a stiff capsule welded into the end of the cable. Since the most resistive portion to flection of any flexible material, such as a cable, tube, or wire is the segment closest to the end, to join a capsule which is stiffer than this material and welded onto its end would only add to the resistance to bending and would adversely effect maneuvering the material through the body.

U.S. Pat. No. 5,084,002 issued to Liprie describes an ultra-thin high dose iridium source included within an oversized hole drilled inside the end of a solid platinum wire. Drilling a hole into a thin wire is very difficult since the maximum depth the hole can be drilled is equal to approximately seven times the outside diameter of the wire. To drill a hole deeper than this is extremely difficult due to the drifting of the drill as it burrows the hole. This drifting can lead to a thinning of the cavity walls which greatly increases the chances of breakage. This breakage is often disastrous, resulting in unwarranted radiation exposure. A larger outside diameter wire will be needed to compensate for the drifting and still allow the walls of the cavity to be thick enough to withstand stress. Unfortunately, this larger diameter wire might be too large to fit into many constricted areas of the body. As described in Liprie '002 one can drill a cavity inside a solid wire, if one starts with an oversize wire and an oversize hole and then the whole assembly is drawn down to the desire diameter of the wire. However, whenever a wire is drawn down, the assembly containing the cavity elongates and the precise positioning of the radioactive core inside the assembly can become very difficult. Additionally, this larger diameter wire would result in less flexibility and may not be able to be maneuvered to the treatment site.

Finally, U.S. Pat. No. 5,282,781 issued to Liprie employs tube, a backbone wire, a pure iridium core and a plug and draws down the entire assembly to form a tight seal between the housing material and the backbone wire and the plug. Without this drawing down of the housing onto the backbone wire, radioactive flakes from the core would migrate throughout the inside of the assembly wire, resulting in unwanted contamination. This "drawing down" step would increase the costs and difficulty of manufacturing the source wire. Furthermore, any "drawing down" step as described in U.S. Pat. No. 5,084,002 and U.S. Pat. No. 5,282,781 would not work on a memory resistant alloy. As soon as a memory resistant alloy had been drawn through a die, the alloy would resume its original shape. If the memory resistant alloy was drawn beyond the threshold of its elasticity, then the memory resistant properties of the alloy would be destroyed.

Thus, there exists a need for a radioactive source wire that has an extremely small diameter and is flexible, yet has sufficient tensile strength to traverse a tortuous route of bends and turns without breaking.

It is an object of the present invention to provide a small diameter source wire that is extremely flexible and will allow the source to travel to the site of treatment without binding.

It is another object of the present invention to provide a source wire that is strong enough to withstand the stresses placed upon the source, as it is maneuvered to and from the site of treatment within the patient, without breaking.

Yet another object of the present invention is to provide an improved source wire design that includes a mechanism for relieving some of the stress encountered by the metal housing tube of the source wire as it is maneuvered to the treatment site.

Still yet another object of the present invention is to provide an improved source wire that exhibits little or no memory retention when bent.

An additional object of the present invention is to provide for improved methods of manufacturing source wires that would decrease the costs and difficulty in manufacturing source wires without sacrificing the quality of the manufactured source wire.

SUMMARY OF THE INVENTION

These and other deficiencies of the prior art are addressed by the present invention which is directed to a flexible source wire for the radiation treatment of disease in which the source wire contains a radioactive core and is easily maneuvered to the site of treatment through various conduits in the body.

A flexible source wire is provided containing a radioactive source that is capable of maneuvering through a tortuous narrow passage to a treatment site within the body. This source wire includes a thin flexible housing tube, housing therein a flexible backbone wire, wherein both the tube and the wire are constructed from a material exhibiting little or no memory retention when bent. A radioactive core is provided in the proximal end (i.e., the treatment end) of the thin flexible housing tube and abuts the proximal end of the backbone wire. Both ends of the source wire are sealed and at least the proximal end of the source wire is rounded to allow ease of movement as it travels through the bends and turns in the body.

The flexible source wire described herein may have a backbone wire that is tapered at the end closest to the radioactive core. The tapered end of the backbone wire terminates next to the radioactive core in a rounded area shaped like a ball. The radioactive core, positioned within the housing tube, may exist openly within the housing tube or may be localized in an open-ended capsule or may be encapsulated by a thin-walled, flexible material or coating that allows the passage of neutrons.

One advantage of the present invention is that it provides a smaller diameter source wire than is currently available.

Another feature and advantage of the present invention is that the source wire has a sufficient tensile strength and flexibility to withstand the stresses encountered when the source wire is maneuvered to the site of treatment.

Yet another feature and advantage of the present invention is that it provides a novel mechanism for relieving some of the stress encountered by the metal housing tube as the source wire is maneuvered to the treatment site.

Still yet another feature and advantage of the present invention is that the source wire is made of a material that can undergo a 1% strain with less than a 1% alteration in its original conformation.

A further feature and advantage of the present invention is that it provides improved methods of manufacturing source wires that will save the manufacturer time and money.

Additional features and advantages of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the claims of the invention.

BRIEF DESCRIPTION OF THE DRAWINGS

For a more complete understanding of the present invention, and the advantages thereof, reference is now made to the following descriptions taken in conjunction with the accompanying drawings, in which:

FIG. 2 is a partial cross-section of another embodiment of a source wire showing a radioactive core enclosed in a capsule within the flexible housing tube;

FIG. 3 is a partial cross-section of another embodiment of the present invention having a radioactive core in an open-ended capsule within a flexible housing tube;

FIG. 4A is a partial cross-section of another embodiment of the present invention having a tapered backbone wire with a rounded area on the proximal tip of the backbone wire;

FIG. 4B shows the embodiment illustrated in FIG. 4A where the backbone wire has altered its shape in response to stress;

FIGS. 5A through C show a diagrammatic view of a source wire and what happens when the flexible housing tube breaks and the backbone wire is not attached to the inner surface of the housing tube;

FIGS. 5D and E show a diagrammatic view of a source wire, with and without a break in the housing tube, where the backbone wire is attached to the inner surface of the housing tube;

DETAILED DESCRIPTION OF THE PREFERRED EMBODIMENTS

The present invention relates to the design and manufacture of improved source wires for delivering radioactivity to a site of treatment within the human body. The invention relates to a novel source wire design that provides improved source wire flexibility and strength such that the improved source wire can survive the stress encountered when it is subjected to the manipulations necessary to maneuver the source wire to and from an internal treatment site for the localized delivery of radiation to diseased tissue. The present invention may be used to treat cancer, stenosis, or other diseases of the body. The use of the present invention in the treatment of stenosis is described in co-pending U.S. patent application entitled "Method and Apparatus for Treating Stenosis," Ser. No. 08/220,681, and is hereby incorporated by reference herein.

Figure 1:
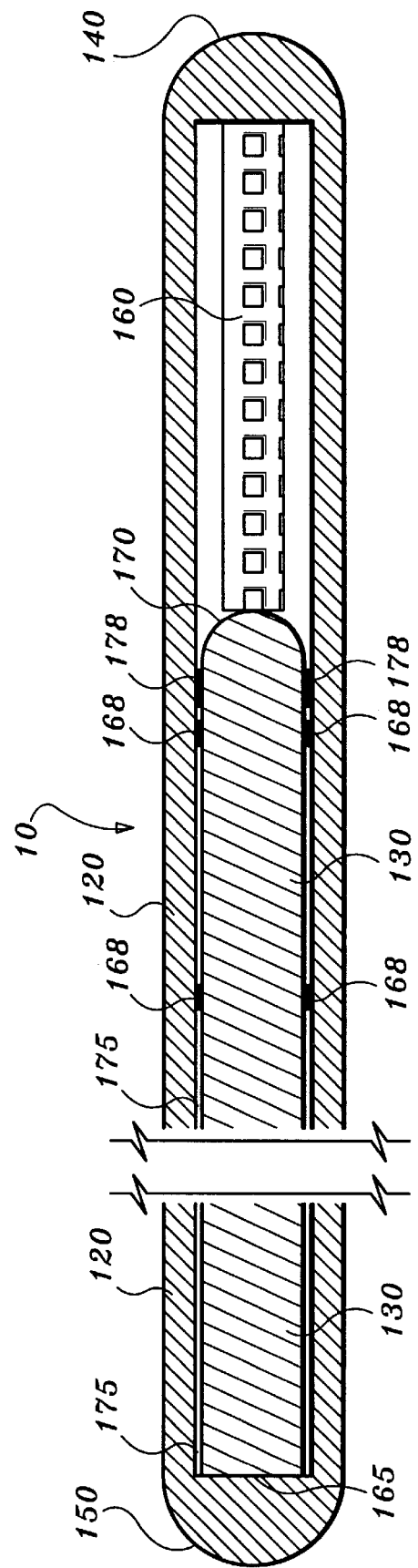
FIG. 1 is a partial cross-section of one embodiment of a source wire showing a backbone wire and a radioactive core enclosed within a flexible housing tube.

Referring now to the drawings, and initially to FIG. 1, it is emphasized that the Figures, or drawings, are not intended to be to scale. For example, purely for the sake of greater clarity in the drawings, wall thickness and spacings are not dimensioned as they actually exist in the assembled embodiments. Furthermore, the lengths of the backbone wire and the radioactive core are illustrated out of proportion to how they actually exist, purely for the sake of clarity.

FIG. 1 illustrates a first embodiment of a source wire 10. Among the components of the source wire 10 is a thin, elongated, flexible metal housing tube 120. Since this housing tube 120 is used to maneuver the radioactive core to a remote treatment site, the length of the tube must be adequate to reach the treatment site when the source wire 10 is inserted through a catheter implanted in a patient's body for that purpose. Typically, tube 120 will have a length of at least 100 cm and may extend for a much greater distance. Additionally, the outside diameter of tube 120 will range from about 0.012" to about 0.018" and is preferably about 0.014". Tube 120 has thin walls, with a wall thickness ranging from about 0.0020" to about 0.0035" and is preferably about 0.0025". The internal diameter of the housing tube ranges from about 0.008" to about 0.014" and is preferably about 0.0093".

Selecting the size of the metal housing tube 120 requires that one balance the increased trauma to the tissue through which source wire 10 will pass, with the increase in tensile strength and elongation of larger tubing. The tubing to be used should be as small as practical and still have the tensile strength, flexibility, and elongation properties necessary to withstand the pressures put upon the source wire while it is maneuvered throughout the body.

Preferably, housing tube 120 is constructed from a material that can accept up to a 1% strain with less than a 1% alteration in its original shape (i.e., a material that exhibits little or no memory retention when bent). Most metals such as stainless steel will incur a permanent alteration in its original shape when subjected to as little as a 0.1% strain. An example of a material that exhibits little or no memory retention when bent is Tinel Alloy BB, a titanium/nickel alloy, manufactured by Raychem Corporation, Menlo Park, Calif. Another commercially available alloy with similar properties is Nitinol® manufactured by Shape Memory Alloys, Sunnyvale, California. Tinel Alloy BB, and other such nickel/titanium alloys, are comprised of about equal quantities of nickel and titanium, such as an alloy composed of about 55% nickel and about 45% titanium.

Tube 120 has two ends, one of which will ultimately constitute the proximal end 140 and the other the distal end 150 of source wire 10. The proximal end 140 should be rounded to facilitate the movement of source wire 10 through the bends and turns of the vasculature, or other treatment sites.

Another component of source wire 10 is a flexible backbone wire 130 which has a diameter slightly less than the inner diameter of housing tube 120, and is preferably about 0.0085" in diameter. Since the backbone wire 130 has a smaller diameter than the inner diameter of the housing tube 120, a small gap 175 will exist between the outer surface of the backbone wire 130 and the inner surface of the housing tube 120. Backbone wire 130 is positioned within the lumen of metal tube 120 from the distal end 150 of tube 120 and extending virtually the entire length of the tube except for a portion of tube 120 at the proximal end which will accommodate the radioactive core 160. Backbone wire 130 will generally be secured to the distal end 150 of housing tube 120 by weld 165, or some other means of attachment such as gluing. In addition, backbone wire 130 may be affixed to the inner surface of housing tube 120 at a variety of attachment sites 168.

An important function of backbone wire 130 is to enhance the flexibility of source wire 10. The outer metal housing tube 120 has a certain degree of flexibility, but in the absence of inner support would tend to bend or buckle and may even collapse when transversing tight turns through a catheter. That tendency is prevented by the presence of the internal backbone wire 130. Thus, the backbone wire 130, like the housing tube 120, must be composed of a very flexible material with sufficient tensile strength to undergo the stress encountered when the source wire 10 is maneuvered to a treatment site. Therefore, backbone wire 130 should be constructed of a material with properties similar to that of housing tube 120. In fact, if the backbone wire 130 is welded to the distal end of tube 120 then the backbone wire 130 and tube 120 should be made of the same material, for example a titanium/nickel alloy as described above.

For ease of initially inserting the backbone wire 130 into the tube 120 and to allow greater pivoting of the assembly while reducing stress to the housing material, the proximal end 170 of the backbone wire 130 is rounded. Other configurations of backbone wire 130 will be discussed in the description of other embodiments of the invention.

A third component of source wire 10 is a radioactive core 160. Radioactive core 160 may be composed of a variety of different radioisotopes such as Ir-192, Cs-137, Co-57, Co-60, Sr-89, Sr-90, P-32, Y-90, Au-198, I-125, Pd-103, Se-75, Ru-106, Yb-169, or Am-241. However, the preferred embodiment of core 160 will consist of a substantially pure iridium, which has been irradiated in a nuclear reactor to produce Ir-192 of a predetermined strength appropriate to its weight. Core 160 has a diameter that is smaller than the inner diameter of housing tube 120. Core 160 is inserted in the proximal end of the lumen of tube 120 and is pushed inward until core 160 abuts the rounded end 170 of backbone wire 130. A plurality of radioactive cores 160 may also be employed in the present invention.

A preferred embodiment of the invention has a radioactive core 160 of at least 20 mm in length that emits about 380 keV of energy. By spreading out the 380 keV emitted over at least a 20 mm distance, the core 160 is directly visible with a fluoroscope. Although the energy emitted by the radioactive core 160 and the length of the source of radioactivity will vary with different embodiments of the invention, the preferred embodiment will have a radioactive core that can be seen with a fluoroscope. This feature provides a distinct advantage over the currently available sources which have a radioactive core of 10 mm or less in length. These point sources emit the equivalent 380 keV of energy in a less diffused manner. Thus the emitted energy hits the fluoroscope directly and overrides its ability to visualize the radioactive source. Therefore, the radioactive cores of currently available source wires are not directly visible with a fluoroscope and must be positioned inside the body without the visual confirmation allowed with the present invention.

A preferred embodiment of the invention has a core 160 that is about 0.005" in diameter. Thus, in this embodiment the core 160 is smaller in diameter than the backbone wire 130 thereby providing increased flexibility to the proximal end of the source wire 10. In fact, when core 160 has a smaller diameter than backbone wire 130, the end of the source wire housing core 160 will have more flexibility than the portion of the source wire containing the backbone wire 130. This increased flexibility at the front end of the source wire will allow the source wire to maneuver easier through tight bends and curves.

Once the core 160 has been inserted into source wire 10 the proximal end 140 of tube 120 is rounded using an arc welder, such as a tungsten inert gas (or TIG) welder. The purpose of the rounded end of source wire 10 is to seal radioactive core 160 within the interior of tube 120 and to facilitate the advancement of the source wire 10 through an implanted catheter to the treatment site.

FIG. 2 illustrates a second embodiment 20 of the present invention. This embodiment is similar in many respects to the embodiment shown in FIG. 1 and will have the same reference numerals as the respective elements pictured in FIG. 1. This embodiment also has an elongated cylindrical metal housing tube 120, similar in dimensions and characteristics to the tube described with respect to FIG. 1. A backbone wire 130, preferably constructed from the same material as the housing tube 120, is introduced to the interior of the housing tube 120 and extends from the distal end 150 thereof to an area positioned several millimeters (preferably about 32 mm) from the proximal end 140 of the tube 120. The backbone wire 130 is provided with rounded end 170 to aid its movement within the tube 120 and to allow greater pivoting of the assembly while reducing stress to the housing material.

A radioactive core 160 is enclosed within a thin-walled capsule 220. This capsule 220 is inserted into tube 120 so that the distal end 230 of capsule 220 abuts the rounded end 170 of the backbone wire 130. The capsule 220 should be flexible and the wall of capsule 220 should be manufactured to a thickness of between 0.001" and 0.0005". This thin capsule 220 should be made of a material that allows the passage of neutrons without obtaining significant radioactivity itself. Thus, should the capsule material become radioactive by neutron flux, the material and any contaminants of that material should have a short half-life as compared to the radioactive core 160. It is important that the capsule 220 should emit less than 10% of the radiation emitted by core 160.

The capsule 220 may be made in a variety of ways. For example, it may be made from a carbon filament sealed with epoxy on both ends, or it may be made of a very thin metallic substance (e.g., titanium, a high purity aluminum such as aluminum 1100, platinum, or the titanium/nickel alloy described previously) with both ends welded, soldered, or glued closed. In a preferred embodiment the iridium will be encapsulated before it is irradiated to form Ir-192 and the capsule 220 will allow the passage of neutrons to irradiate the core 160.

Once the capsule 220 has been positioned within housing tube 120 adjacent to backbone wire 130 an optional plug 250 may be inserted next to the proximal end 225 of capsule 220. When the desired components have been appropriately positioned, the proximal end 140 of source wire 20 is sealed and rounded as described above. A preferred embodiment of the invention will seal proximal end 140 by fusing the proximal end of tube 120 with an arc welder (when plug 250 is not incorporated into the source wire). Alternatively, the proximal end of source wire 20 can be sealed and rounded by welding, gluing, or soldering the plug 250 to the proximal end of tube 120 and rounding the proximal end with a router, grinder, sander, etc. to achieve a rounded end 140.

The preferred embodiment of capsule 220 will be rounded on both ends. The purpose of having a rounded distal end 230 of capsule 220 is to allow greater pivoting of the source wire 20 while reducing stress to the housing material at the juncture of backbone wire 130 and capsule 220. Although the preferred embodiment has a single capsule 220, a plurality of capsules could be employed in the present invention, or a plurality of cores 160 could be incorporated within a single capsule 220.

FIG. 3 illustrates an additional embodiment of a flexible source wire 30, this source wire is similar in most respects to the embodiments shown in FIGS. 1 and 2. In this embodiment, similar elements in FIG. 1 will have the same reference numerals as their respective elements in FIG. 3. FIG. 3 shows a source wire in which radioactive core 160 is located within an open-ended capsule 330. This capsule 330 is like capsule 220, except that it is open on the end proximate to the proximal end of the source wire 30. When open-ended capsule 330 is used, an optional plug 350 may be placed over the open end of capsule 330 before it is sealed. Open ended capsule 330 may be sealed by welding the proximal end of the capsule 330 to the proximal end of the tube 120, if the capsule 330 and the tube 120 are made of the same material. Alternatively, if plug 350 is used then plug 350 may be composed of the same material as tube 120 and may thus be welded to the proximal end 140 of tube 120. However, alternative means of sealing the proximal end of capsule 330 and tube 120 may also be employed.

Open-ended capsule 330, like capsule 220 shown in FIG. 2, is positioned adjacent to rounded end 170 of backbone wire 130. The distal end 340 of open-ended capsule 330 is rounded to facilitate bending of source wire 30 at the juncture of backbone wire 130 and open-ended capsule 330.

Figure 7:
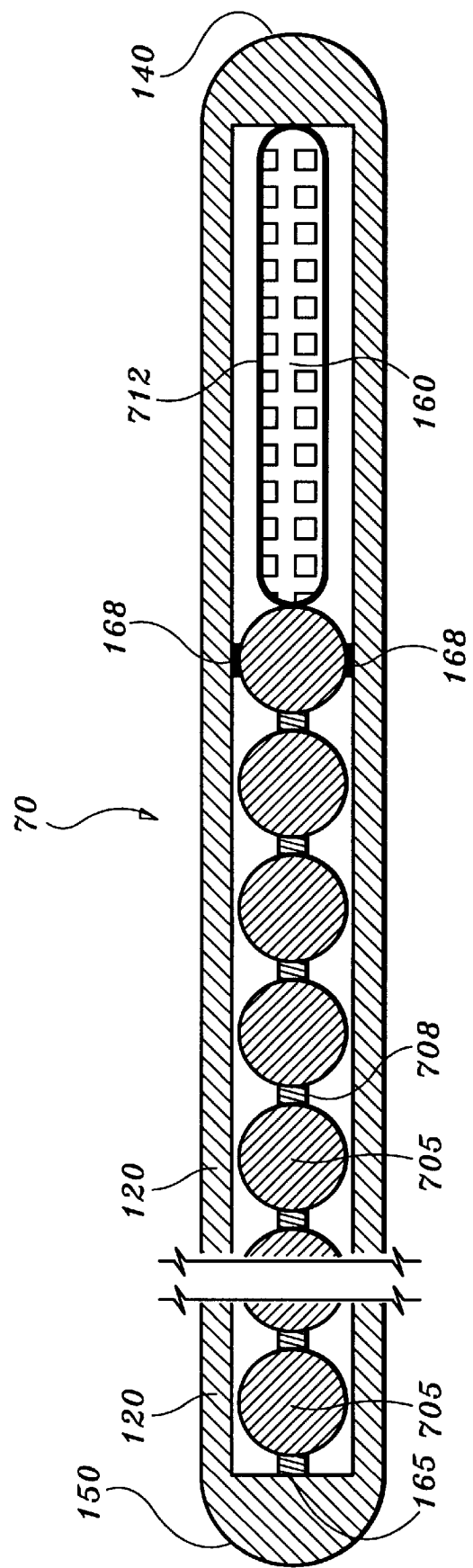
FIG. 7 shows a partial cross-section of a source wire having a backbone, comprised of a number of balls linked together by a thin wire, and a radioactive core coated with a neutron permeable material within a flexible housing tube.

FIG. 7 illustrates an alternative embodiment of the source wire where the backbone wire consists of a series of ball-like structures 705 interconnected with short lengths of a thin wire 708. This configuration provides increased flexibility throughout the length of the source wire with each ball acting as a pivoting agent and relieving stress to the wall of housing tube 120. FIG. 7 also shows radioactive source 160 having a thin coating 712 of a neutron permeable material. The coating 712 may be an electroplated coating of a material such as gold, titanium, platinum, ect. Coating 712 may also be made of non-metallic materials such as a hardening agent (e.g., glue or acrylic). Coating 712 may be applied to core 160 by brushing, dipping, painting or molecularly bonding the coating material to the outer surface of core 160. Coating 712 will completely cover the outside surface of core 160 and will function to prevent the flaking of the radioactive core 160.

FIG. 4A shows a preferred embodiment of the present invention. This embodiment of a flexible source wire 40 is similar in many respects to the embodiments shown in FIGS. 1 and 3. Therefore the elements in FIG. 4 corresponding to similar elements in FIGS. 1 and 3 are given the same reference numerals as their respective elements in FIGS. 1 and 3. The embodiment illustrated in FIG. 4A has a different configuration of its backbone wire to that shown in any of the other embodiments and includes an untapered portion 430, a tapered portion 440, and a rounded area 450. The backbone wire of source wire 40 is tapered at its proximal end. Backbone wire 420 is tapered over approximately the last 0.5" to 2.0" of its proximal end. The taper 440 goes from a 100% width of the untapered backbone wire 430 to about 30% to 60% of the width of the untapered backbone wire 430 as the taper extends toward the proximal end of source wire 40. Taper 440 of backbone wire 420 terminates in a rounded area 450, where rounded area 450 approximates the shape of a ball. This configuration allows the source wire 40 to release some of the stress on the outer wall of housing tube 120 when the source wire bends to transverse a tight corner. In fact the stress placed on rounded area 450 and translated to backbone wire 420 will cause the backbone wire to crumple along the tapered area as illustrated in FIG. 4B. However, since the backbone wire 420 is made from a flexible material that exhibits little or no memory retention when it is bent, or more specifically a material that can accept up to a 1% strain with less than a 1% alteration in its original shape, the backbone wire 420 will resume its original shape when the stress is removed and the source wire traverses a straight passage. The novel design of backbone wire 420 increases the flexibility and maneuverability of the source wire 40, as well as decreasing the stress on the wall of housing tube 120. By decreasing the stress on housing tube 120, this backbone design allows the use of a smaller diameter source wire than is currently available.

An optional feature of each of the source wire embodiments is to attach the backbone wire 130 or 420 to the inner surface of the housing tube 120 by welding, fusing, soldering, gluing, etc. Sites of attachment 168 are shown in FIGS. 1–4. These sites of attachment 168 provide an internal safety device that insures that if the housing tube 120 were to break that the radioactive core 160 would not separate from the backbone wire 130 and could be retracted from the patient. FIGS. 5A through C illustrate what happens if the housing tube 120 breaks and the backbone wire 130 is not attached to the inner surface of tube 120. FIG. 5B shows where tube 120 has broken and FIG. 5C shows how the radioactive core 160 would be left in the patient when the backbone wire 130 was retracted. In contrast, when backbone wire 130 is attached to the inner surface of tube 120 at attachment sites 168, as seen in FIG. 5D, if the metal housing tube 120 breaks at any point distal to attachment sites 168 then the radioactive core 160 will still be attached to the backbone wire 130 and will be retracted from the patient when the backbone wire 130 is withdrawn, as seen in FIG. 5E.

Another optional feature of the source wires described herein is to provide a seal 178 between the inner surface of housing tube 120 and backbone wire 130 by welding, fusing, soldering, gluing, etc. the backbone wire to the interior surface of housing tube 120. This seal 178 could also serve as an attachment site 168.

Seal 178 may be made by a number of methods. One such method would be to thread the backbone wire 130 through the length of the housing tube. The distal end of the wire would be marked at the point where the proximal end of the wire is flush with the proximal end of the housing tube 120. The backbone wire would then be pushed forward and a small amount of slow drying epoxy placed around the circumference of the backbone wire 130 about two centimeters from the proximal end of the wire. Once the epoxy is added to the wire, the wire would be pulled back into the housing tube until the mark on the distal end extended from the distal end of the housing tube the appropriate distance, preferably about 32 mm. The backbone wire would then be cut flush with the distal end of the wire and welded to the housing tube to seal the distal end of the backbone wire 130. Any glue adhering to the internal surface of the proximal portion of the housing tube, where the epoxied backbone wire was drawn through the housing tube, would be reemed out before the radioactive core 160 was inserted into the backbone wire.

An alternative method of producing a seal 178 would be to follow the procedure described above, except to allow the epoxy to dry before drawing the proximal end of the backbone wire back into the housing tube. The epoxy ring would then be ground or sanded to fit snugly within the housing tube 120.

Figure 4C:
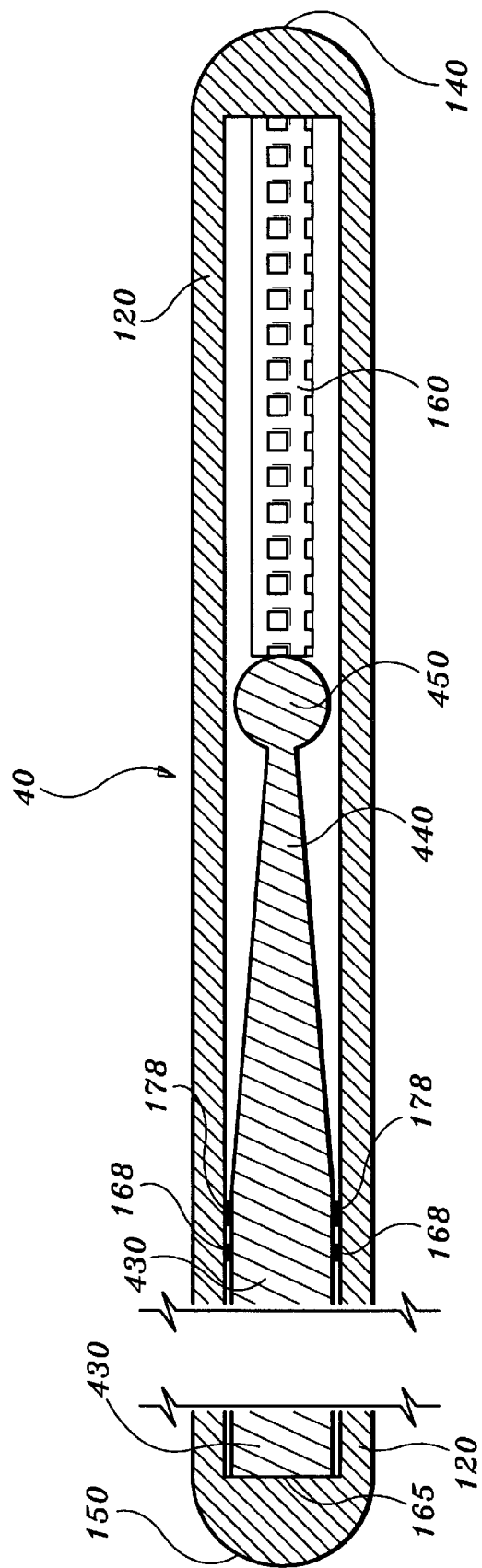
FIG. 4C shows an embodiment having the tapered backbone wire illustrated in FIG. 4A but where the radioactive core is placed directly into the housing tube rather than in an open-ended capsule.

Seal 178 would encircle backbone wire 130 closing off gap 175 and thereby preventing any "flakes" from the radioactive core 160 from migrating through gap 175 between the backbone wire 130 and the inner surface of housing tube 120. Seal 178 is typically incorporated into embodiments of the invention where radioactive core 160 is not enclosed in a capsule or encapsulated as seen in FIG. 1 and FIG. 4C.

Seal 178 and attachment site 168 are produced in a similar manner. The major difference between seal 178 and attachment site 168 is that attachment site 168 may only attach a small segment of the diameter of backbone wire 130 to the inner surface of the housing tube 120. Thus, gap 175 may not be totally closed all around the backbone wire 130 when the backbone wire 130 is only attached to the inner surface of tube 120 at a small portion of its circumference as may happen in forming an attachment site.

Yet another optional feature of the source wires described herein (but not shown) would be to coat the exterior surface of the source wire with a non-oxidizing agent, such as gold. In one embodiment of the present invention, a thin gold layer (from approximately 1 to 10 microns thick) would be electroplated over the outer surface of metal tube 120, or at least that portion of the surface overlying the radioactive core 160 and preferably extending over the proximal end 140 of the source wire. Furthermore, the gold coating of the source wire would preferably be done prior to loading the radioactive core 160 into housing tube 120.

The fabrication of the source wires shown in FIGS. 1–4 is described below. The first step in the manufacture of the described source wires is to obtain the metal tubing that will be used to make the housing tube 120. Once the tubing is acquired, a calibrated micrometer for measuring the outside diameter and calibrated rods for measuring the inside diameter are used to validate that the tubing meets the manufacturer's specifications. The preferred embodiment of the present invention uses Tinel Alloy BB tubing of an external diameter of 0.014 from Raychem Corporation.

The backbone wire is also commercially obtained. For the backbone wire 130, a solid wire of Tinel Alloy BB is ordered that has a diameter of 0.0085". Rounded end 170 of backbone wire 130 is produced using the heat from a TIG welder.

Backbone wire 420 is made by taking the Tinel Alloy BB wire ordered and grinding it down with an electric sander. The wire is held in a pin vise and rotated while grinding to taper the wire. The tapering can be done automatically or manually. The tapered end is examined under a microscope and with a micrometer to ensure that it is tapered sufficiently (i.e., with the right degree of reduction in the diameter of the wire and that it is evenly tapered). Once the appropriate taper of backbone wire 420 is achieved then the rounded area 450 is formed on the tapered end of backbone wire 420. The rounded area 450 is formed by heating the tapered end of backbone wire 420 with an arc welder after placing the tapered end of backbone wire 420 into a heat sink (preferably made of aluminum, copper, brass, or any other material that will absorb heat away from the protected object) at a predetermined distance above the heat sink. The dimensions of the rounded area 450, or ball, will be determined by the gap between the top of the wire and the bottom of the tungsten welding rod and by the length of the wire above the heat sink 650 that is exposed to the heat of the TIG welder. Typically the wire is placed 0.025" (or about 0.1 mm) above the heat sink 650 using a feeler gauge. A feeler gauge is also used to set a gap of about 0.030" between the top of the wire and the bottom of the welding rod. Once the tapered end of backbone wire 420 is placed the proper distance from the heat sink 650 and welding rod, the tapered end of the wire 420 is exposed to a TIG welder. The metal above the heat sink 650 will melt and form a rounded area 450. Typically, the rounded area will be a ball of about 0.0085" in diameter, or of a similar diameter as the untapered backbone wire.

Next a wire of about 32 mm in length is threaded into the lumen of the housing tube at what will become the proximal end 140 of the tube 120. The backbone wire 130 or 420 is then threaded through the distal end of the lumen of the housing tube 120 until it reaches the 32 mm wire placed at the proximal end of the tube 120. The backbone wire is marked where it exits the distal end of the tube 120. The backbone wire is then cut at the mark and is rethreaded into the lumen of the housing tube 120 so that the cut end of backbone wire 130 or 420 is flush with the distal end of housing tube 120. The distal end of the wire is then welded to the distal end of tube 120 with a TIG welder. This provides a rounded end 150 of the source wire that has a slightly larger diameter than tube 120 and provides an end that can be inserted into an afterloader, where the source wire can be held in place by the rounded end 150 and a set screw that is tightened into the wire just below the rounded end 150.

Next the 32 mm wire that was placed in the proximal end of housing tube 120 is removed. The proximal end of the housing tube 120 is then set about 0.025" above a heat sink 650. The heat sink 650 is also used as a clamping device to hold the wire in place. A gap of about 0.035" is set between the top of the housing tube 120 and the bottom of the welding rod. Then an iridium fiber, which has been irradiated in a nuclear reactor to the desired radioactivity and held for 11 to 14 days to purge the iridium fiber of any short lived radioactive contaminants, is removed from its container. The iridium fiber may or may not be encapsulated as described above. The iridium fiber is preferably 30 mm in length and about 0.005" in outside diameter.

The radioactive iridium fiber is loaded into the housing tube 120 using a funnel. The iridium fiber is made flush with the bottom of the funnel. A small rod, having a proper length and outside diameter, is used to countersink the Ir-192 about 2 mm from the top of the housing tube 120. The funnel is then removed. The assembly of the radioactive core 160 into the housing tube 120 is done using hand manipulators behind a leaded glass with lead shields so that the human assembler is not exposed to radiation. The forceps, funnel and heat sink used during the process that may have touched the radioactive core 160 must be decontaminated or disposed of properly.

Figure 6:
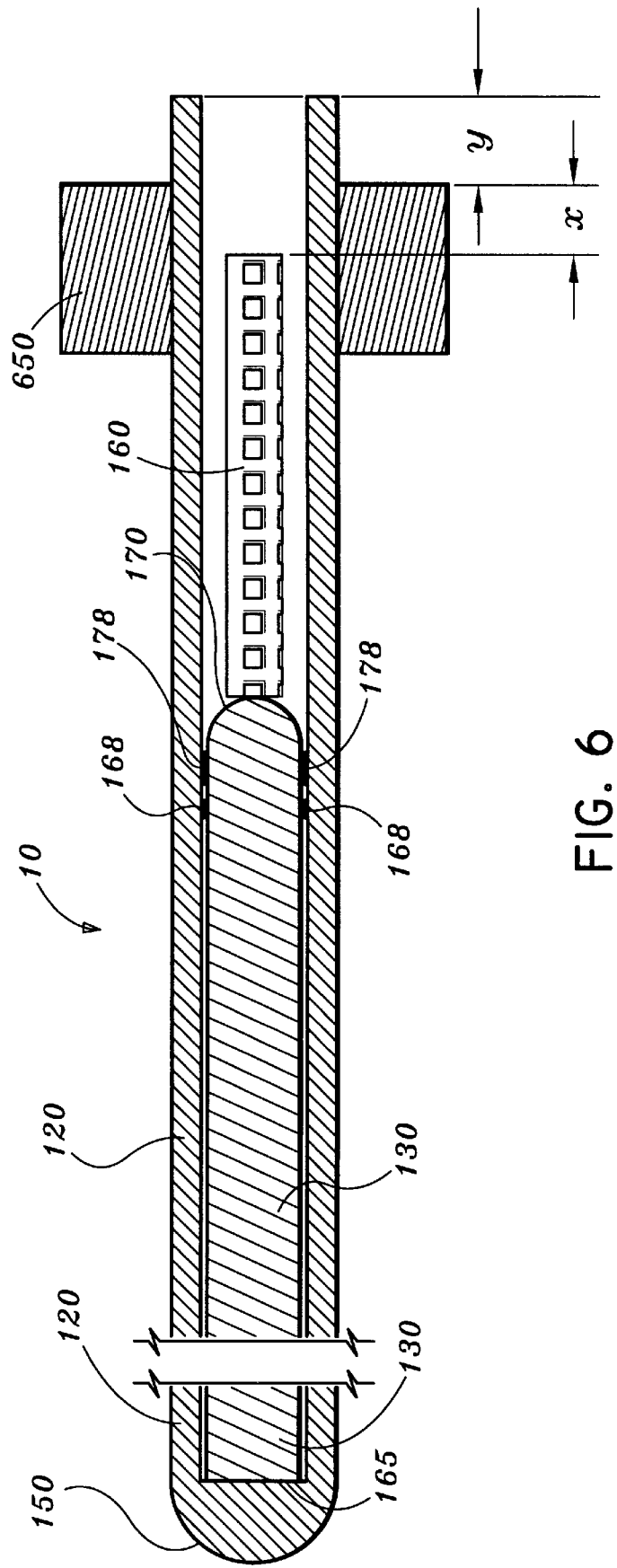
FIG. 6 shows a partial cross-section of a source wire positioned in a heat sink before its proximal end is sealed.

Once the iridium fiber, or encapsulated fiber, is set in the proximal end of the housing tube 120, as illustrated in FIG. 6, the exposed proximal end of tube 120 is subjected to the heat of a TIG welder. This fuses the exposed end of the housing tube or welds it to plug 350, if 350 plug is present. Without the heat sink the heat would go directly to the iridium fiber and would oxidize, vaporize or fracture the iridium core 160 causing contamination of the outside surface of the source wire rendering it unusable. However, if the housing tube is placed a distance Y above the heat sink 650 and the radioactive core 160 is placed a distance X below the top of the heat sink 650 then the TIG welder will cause the tube 120 to seal the proximal end 140 of the source wire without affecting the radioactive core 160. As long as the distances between the top of the housing tube and the heatsink, as well as the top of the housing tube and the bottom of the welding rod are correct, a rounded surface ranging from about 0.016" to about 0.018" in diameter results. The size of the rounded area is verified with gauges so that the resulting source wire will fit into the internal diameter of the positioning catheter that is used to properly place the radioactive source wire at the treatment site. Once the source wire has been fabricated, it is wiped clean with swabs and loaded into a lead container to await use in a patient.

Having described several embodiments of the new and improved flexible source wire for radiation treatment in accordance with the present invention, it is believed that other modifications, variations and changes will be suggested to those skilled in the art in view of the description set forth above. It is therefor to be understood that all such variations, modifications and changes are believed to fall within the scope of the invention as defined in the appended claims.

What is claimed is:

1. A source wire for radiation treatment of disease within a body comprising:
   a generally cylindrical elongated housing tube having an outer surface, an interior surface, a distal end, a rounded proximal end, and an original configuration, said tube constructed of a material that can accept up to a 1% strain with less than a 1% permanent alteration in said tube's original configuration;
   a flexible backbone wire having a first end and a second end, said wire encased and secured within said housing tube wherein said first end is adjacent to said distal end of said tube and said second end is rounded; and
   means for emitting radioactivity, said radioactive means localized within said housing tube adjacent to said rounded second end of said wire and proximate to said proximal end of said housing tube, wherein said proximal end is sealed to prevent the release of said radioactive means.

2. The source wire of claim 1, wherein said radioactive means has a smaller outer diameter than said flexible backbone wire.

3. The source wire of claim 1, wherein said housing tube is made of a titanium/nickel alloy.

4. The source wire of claim 3, wherein said titanium/nickel alloy is composed of about 55% nickel and about 45% titanium.

5. The source wire of claim 1, wherein an outer diameter of said housing tube is from about 0.012 in. to about 0.018 in.

6. The source wire of claim 1, wherein said backbone wire is made of the same material as said housing tube.

7. The source wire of claim 1, wherein the first end of said backbone wire is attached to the distal end of said housing tube.

8. The source wire of claim 1, wherein said backbone wire is affixed to said interior surface of said housing tube at more than one site.

9. The source wire of claim 1, wherein said outer surface of said housing tube is coated with a non-oxidizing agent.

10. The source wire of claim 9, wherein said non-oxidizing agent is gold.

11. The source wire of claim 1, wherein said radioactive means can be visualized with a flurorscope.

12. The source wire of claim 1, wherein said radioactive means comprises Ir-192.

13. The source wire of claim 1, wherein said radioactive means is at least 20 mm in length.

14. The source wire of claim 1, wherein said radioactive means is encapsulated within a thin-walled neutron permeable material prior to being localized within said housing tube.

15. The source wire of claim 14, wherein said encapsulating material includes gold, acrylic, glue, epoxy, carbon, titanium, platinum, nickel, or high purity aluminum.

16. The source wire of claim 1, further comprising a sealing device located between said backbone wire and said inner surface of said housing tube; said sealing device encircling said backbone wire to prevent radioactive material from migrating along said housing tube distal to said sealing device.

17. The source wire of claim 1, wherein said backbone wire includes an untapered portion and a tapered region distal to said second end of said backbone wire.

18. The source wire of claim 17, wherein said tapered region of said backbone wire extends from about 0.5 inches to about 2.0 inches proximate to said rounded end.

19. The source wire of claim 18 wherein said rounded second end approximates the shape of a ball.

20. The source wire of claim 1, wherein said backbone wire comprises a series of rounded ball-like sections interconnected by a wire having a smaller diameter than said ball-like sections.

21. The source wire of claim 1, wherein said radioactive means is a single radioactive source.

22. The source wire of claim 1, wherein said radioactive means comprises a plurality of radioactive sources.

23. The source wire of claim 1, further comprising means for preventing radioactive particles released from the radioactive source from entering the space between the backbone wire and and the interior of said housing tube.

24. The source wire of claim 23 wherein said preventive means includes a seal between said backbone wire and said housing tube.

25. A source wire for radiation treatment of disease within a body comprising:

a generally cylindrical elongated housing tube having an outer surface, an interior surface, a distal end, a rounded proximal end, and an original configuration, said tube constructed of a material that can accept up to a 1% strain with less than a 1% permanent alteration in said tube's original configuration;

a flexible backbone wire having a first end and a second end, said wire encased and secured within said housing tube wherein said first end is adjacent to said distal end of said tube;

means for reducing stress at said second end of said backbone wire when stress is applied to said second end; and means for emitting radioactivity, said radioactive means localized within said housing tube adjacent to a rounded second end of said wire and proximate to said proximal end of said housing tube, wherein said proximal end is sealed to prevent the release of said radioactive means.

26. The source wire of claim 25 wherein said stress reducing means includes a tapered region intermediate said rounded second end of said backbone wire and said first end of said backbone wire, said rounded end being adjacent to said radioactive means and attached to said tapered region of said backbone wire.

27. A source wire for radiation treatment of disease within a body comprising:

a generally cylindrical elongated housing tube having an outer surface, an interior surface, a distal end, a rounded proximal end, and an original configuration, said tube constructed of a material that can accept up to a 1% strain with less than a 1% permanent alteration in said tube's original configuration;

a flexible backbone wire having a first end and a second end, said wire encased and secured within said housing tube wherein said first end is adjacent to said distal end of said to tube and said second end is rounded; and a capsule localized within said housing tube adjacent to said rounded second end of said wire and proximate to said proximal end of said housing tube;

means for emitting radioactivity, said radioactive means situated within said capsule; and wherein said proximal end of said housing tube is seated to prevent the release of said radioactive means.

28. The source wire of claim 27, wherein said radioactive means has a smaller outer diameter than said flexible backbone wire.

29. The source wire of claim 27, wherein said housing tube is made of a titanium/nickel alloy.

30. The source wire of claim 29, wherein said titanium/nickel alloy is composed of about 55% nickel and about 45% titanium.

31. The source wire of claim 27, wherein an outer diameter of said housing tube is from about 0.012 in. to about 0.018 in.

32. The source wire of claim 27, wherein said backbone wire is made of the same material as said housing tube.

33. The source wire of claim 27, wherein the first end of said backbone wire is attached to the distal end of said housing tube.

34. The source wire of claim 27, wherein said backbone wire is affixed to said interior surface of said housing tube at more than one site.

35. The source wire of claim 27, wherein said outer surface of said housing tube is coated with a non-oxidizing agent.

36. The source wire of claim 35, wherein said non-oxidizing agent is gold.

37. The source wire of claim 27, wherein said radioactive means is radiopaque for visualizing said radioactive means with a fluoroscope.

38. The source wire of claim 27, wherein said radioactive means comprises Ir-192.

39. The source wire of claim 27, wherein said radioactive means is at least 20 mm in length.

40. The source wire of claim 27, wherein said radioactive means is encapsulated within a thin-walled neutron permeable material prior to being localized within said housing tube.

41. The source wire of claim 40, wherein said encapsulating material includes gold, acrylic, glue, epoxy, carbon, titanium, platinum, nickel, or high purity aluminum.

42. The source wire of claim 27, further comprising a sealing device located between said backbone wire and said inner surface of said housing tube; said sealing device encircles said backbone wire to prevent radioactive material from migrating along said housing tube distal to said sealing device.

43. The source wire of claim 27, wherein said backbone wire includes an untapered portion and a tapered region distal to said second end of said backbone wire.

44. The source wire of claim 43, wherein said tapered region of said backbone wire extends from about 0.5 inches to about 2.0 inches proximate to said rounded area.

45. The source wire of claim 27, wherein said backbone wire comprises a series of round-ed ball-like sections interconnected by a wire having a smaller diameter than said ball-like sections.

46. The source wire of claim 27, wherein said radioactive means is a single radioactive source.

47. The source wire of claim 27, wherein said radioactive means comprises a plurality of radioactive sources.

48. A source wire for radiation treatment of disease within a body comprising:

a generally cylindrical elongated housing tube having an outer surface, an interior surface, a distal end, a rounded proximal end, and an original configuration, said tube constructed of a material that can accept up to a 1% strain with less than a 1% permanent alteration in said tube's original configuration;

a flexible backbone wire having a first end and a second end, said wire encased and secured within said housing tube wherein said first end is adjacent to said distal end of said tube;

means for reducing stress at said second end of said backbone wire when stress is applied to said second end;

a capsule localized within said housing tube adjacent to said rounded second end of said wire and proximate to said proximal end of said housing tube;

means for emitting radioactivity, said radioactive means situated within said capsule; and wherein said proximal end of said housing tube is seated to prevent the release of said radioactive means.

49. The source wire of claim 48 wherein said stress reducing means includes a tapered region intermediate a rounded area on said second end of said backbone wire and said first end of said backbone wire, said rounded area being adjacent to said radioactive core and attached to said tapered region of said backbone wire.

50. A source wire for radiation treatment of disease within a body comprising:

a generally cylindrical elongated housing tube having an outer surface, an interior surface, a distal end, a rounded proximal end, and an original configuration, said tube constructed of a material that can accept up to a 1% strain with less than a 1% permanent alteration in said tube's original configuration;

a flexible backbone wire having a first end and a second end, said wire encased and secured within said housing tube wherein said first end is adjacent to said distal end of said tube and said second end is rounded; and an encapsulated radioactive core localized within said housing tube adjacent to said rounded second end of said wire and proximate to said proximal end of said housing tube, wherein said proximal end of said housing tube is sealed to prevent the release of said radioactive core.

51. The source wire of claim 50, wherein said radioactive means has a smaller outer diameter than said flexible backbone.

52. The source wire of claim 50, wherein said housing tube is made of a titanium/nickel alloy.

53. The source wire of claim 52, wherein said titanium/nickel alloy is composed of about 55% nickel and about 45% titanium.

54. The source wire of claim 50, wherein an outer diameter of said housing tube is from about 0.012 in. to about 0.018 in.

55. The source wire of claim 50, wherein said backbone wire is made of the same material as said housing tube.

56. The source wire of claim 50, wherein the first end of said backbone wire is attached to the distal end of said housing tube.

57. The source wire of claim 50, wherein said backbone wire is affixed to said interior surface of said housing tube at more than one site.

58. The source wire of claim 50, wherein said outer surface of said housing tube is coated with a non-oxidizing agent.

59. The source wire of claim 50, wherein said non-oxidizing agent is gold.

60. The source wire of claim 50, wherein said radioactive means is radiopaque for visualizing said radioactive means with a fluoroscope.

61. The source wire of claim 50, wherein said radioactive means comprises Ir-192.

62. The source wire of claim 50, wherein said radioactive means is at least 20 mm in length.

63. The source wire of claim 50, wherein said radioactive means is encapsulated within a thin-walled neutron permeable material prior to being localized within said housing tube.

64. The source wire of claim 63, wherein said encapsulating material includes gold, acrylic, glue, epoxy, carbon, titanium, platinum, nickel, or high purity aluminum.

65. The source wire of claim 50, further comprising a sealing device located between said backbone wire and said inner surface of said housing tube; said sealing device encircles said backbone wire to prevent radioactive material from migrating along said housing tube distal to said sealing device.

66. The source wire of claim 50, wherein said backbone wire includes an untapered portion, a tapered region, and a rounded area, said rounded area adjacent to said radioactive means.

67. The source wire of claim 66, wherein said tapered region of said backbone wire extends from about 0.5 inches to about 2.0 inches proximate to said rounded area.

68. The source wire of claim 50, wherein said backbone wire comprises a series of rounded ball-like sections interconnected by a wire having a smaller diameter than said ball-like sections.

69. The source wire of claim 27, wherein said radioactive means is a single radioactive source.

70. The source wire of claim 27, wherein said radioactive means comprises a plurality of radioactive sources.

71. A source wire for radiation treatment of disease within a body comprising:

a generally cylindrical elongated housing tube having an outer surface, an interior surface, a distal end, a rounded proximal end, and an original configuration, said tube constructed of a material that can accept up to a 1% strain with less than a 1% permanent alteration in said tube's original configuration;

a flexible backbone wire having a first end and a second end, said wire encased and secured within said housing tube wherein said first end is adjacent to said distal end of said tube;

means for reducing stress at said second end of said backbone wire when stress is applied to said second end; and an encapsulated radioactive core localized within said housing tube adjacent to said rounded second end of said wire and proximate to said proximal end of said housing tube, wherein said proximal end of said housing tube is sealed to prevent the release of said radioactive core.

72. The source wire of claim 71, wherein said stress reducing means includes a tapered region intermediate a rounded area on said second end of said backbone wire and said first end of said backbone wire, said rounded area being adjacent to said radioactive core and attached to said tapered region of said backbone wire.

73. A source wire for radiation treatment of disease within a body comprising:

a generally cylindrical elongated housing tube having an outer surface, an interior surface, a distal end, and a rounded proximal end, said tube constructed of a nickel/titanium alloy;

a flexible backbone wire having a first end and a second end, said wire encased within said housing tube wherein said first end is attached to said distal end of said tube and said second end is rounded and adjoins a tapered area of said backbone wire, said backbone wire being affixed to said interior surface of said housing tube at one or more points; and a radioactive core localized within said housing tube adjacent to said rounded second end of said wire and proximate to said proximal end of said housing tube, wherein said radioactive core has a smaller diameter than said backbone wire; and wherein said proximal end of said housing tube is sealed to prevent the release of said radioactive core.

74. The source wire of claim 73, wherein an outer diameter of said housing tube is from about 0.012 in. to about 0.018 in.

75. The source wire of claim 73, wherein said backbone wire is made of the same material as said housing tube.

76. The source wire of claim 73, wherein said outer surface of said housing tube is coated with a non-oxidizing agent.

77. The source wire of claim 76, wherein said non-oxidizing agent is gold.

78. The source wire of claim 73, wherein said radioactive means is radiopaque for visualizing said radioactive means with a fluoroscope.

79. The source wire of claim 73, wherein said radioactive means comprises Ir-192.

80. The source wire of claim 73, wherein said radioactive means is at least 20 mm in length.

81. The source wire of claim 73, wherein said radioactive means is encapsulated within a thin-walled neutron permeable material prior to being localized within said housing tube.

82. The source wire of claim 81, wherein said encapsulating material includes gold, acrylic, glue, epoxy, carbon, titanium, platinum, nickel, or high purity aluminum.

83. The source wire of claim 73, further comprising a sealing device located between said backbone wire and said inner surface of said housing tube; said sealing device encircles said backbone wire to prevent radioactive material from migrating along said housing tube distal to said sealing device.

84. The source wire of claim 73, wherein said tapered region of said backbone wire extends from about 0.5 inches to about 2.0 inches proximate to said rounded area.

85. The source wire of claim 73, wherein said radioactive means is a single radioactive source.

86. The source wire of claim 73, wherein said radioactive means comprises a plurality of radioactive sources.

87. The source wire of claim 73, wherein said housing tube is made of a titanium/nickel alloy.

88. The source wire of claim 81, wherein said titanium/nickel alloy is composed of about 55% nickel and about 45% titanium.

89. In a source wire for delivery of a radioactive source to a site requiring treatment within a patient's body, in which an elongated housing tube containing a flexible non-radioactive backbone wire and a radioactive source is used to advance and withdraw the radioactive source to the desired location in the patient's body, the improvement comprising a means for increasing the flexibility of said source wire at the junction of said backbone wire and said radioactive source, wherein said means for increasing the flexibility of said source wire includes providing the backbone wire with a tapered proximal end terminating in a ball.

90. The source wire of claim 89 wherein said means for increasing flexibility is formed on said backbone wire.

91. In an elongated source wire for delivery of a radioactive source to a site requiring treatment within a patient's body, in which a substantially elongated housing tube containing a substantially elongated flexible backbone wire and a radioactive source is used to advance and withdraw the radioactive source to the desired location in the patient's body, the improvement comprising a safety mechanism to prevent the radioactive source and a portion of the substantially elongated housing tube from separating from the substantially elongated backbone wire if the housing tube is broken.

92. The source wire of claim 91 wherein said safety mechanism includes at least one site of attachment.

93. In a source wire for delivery of a radioactive source to a site requiring treatment within a patient's body, in which an elongated housing tube containing a flexible backbone wire and a radioactive source is used to advance and withdraw the radioactive source to the desired location in the patient's body, the improvement comprising means for preventing the particles released from the radioactive source from entering the space between the backbone wire and the housing tube wherein said means for preventing is a circumferential weld formed between said backbone wire and an inner surface of said housing.

94. A source wire for radiation treatment of disease within a body comprising:

a flexible housing;

a flexible backbone wire having a first end and a rounded second end, said backbone wire encased within said housing; and means for emitting radiation within said housing and adjacent to said rounded second end of the flexible backbone wire.

95. A source wire according to claim 94 wherein said radiation emitting means is a radioactive core approximately 20 mm in length.

96. A source wire according to claim 95 wherein said radioactive core is radiopaque for visualizing said radioactive core in the patient's body with a fluoroscope.

97. A source wire for radiation treatment of disease within a body comprising:

a flexible housing;

a flexible backbone wire having a first end and a rounded second end, said backbone wire encased within said housing; and a radiation source adjacent to said rounded second end of the flexible backbone wire.

98. A source wire according to claim 97 wherein said radiation source is approximately 20 mm in length.

* * * * *